US008425857B2

(12) United States Patent
Glazer et al.

(10) Patent No.: US 8,425,857 B2
(45) Date of Patent: Apr. 23, 2013

(54) SYSTEM AND METHOD FOR PROCESSING WASTE MATERIAL

(75) Inventors: Sanford A. Glazer, Potomac, MD (US); William D. Norton, Baltimore, MD (US)

(73) Assignee: Red Bag Solutions, Baltimore, MD (US)

( * ) Notice: Subject to any disclaimer, the term of this patent is extended or adjusted under 35 U.S.C. 154(b) by 0 days.

(21) Appl. No.: 13/099,073

(22) Filed: May 2, 2011

(65) Prior Publication Data

US 2011/0268606 A1 Nov. 3, 2011

Related U.S. Application Data

(60) Provisional application No. 61/330,327, filed on May 1, 2010.

(51) Int. Cl.
*A61L 2/16* (2006.01)
(52) U.S. Cl.
USPC .......................................................... 422/292
(58) Field of Classification Search .................. 422/292, 422/22
See application file for complete search history.

(56) References Cited

U.S. PATENT DOCUMENTS

| | | | |
|---|---|---|---|
| 3,310,241 A | 3/1967 | Wandel | |
| 5,078,965 A | 1/1992 | Pearson | |
| 5,116,574 A | 5/1992 | Pearson | |
| 5,277,869 A | 1/1994 | Glazer et al. | |
| 5,427,737 A | 6/1995 | Glazer et al. | |
| 5,431,861 A | 7/1995 | Nagahiro et al. | |
| 5,520,888 A | 5/1996 | Berndt | |
| 5,582,793 A | 12/1996 | Glazer et al. | |
| 5,820,541 A | 10/1998 | Berlanga Barrera | |
| 6,494,391 B2 | 12/2002 | Mosenson et al. | |
| 6,605,750 B1 | 8/2003 | Bessho et al. | |
| 6,955,758 B2 | 10/2005 | Yamazaki et al. | |
| 7,550,111 B2 | 6/2009 | Klaptchuk | |
| 2006/0124541 A1 | 6/2006 | Logan et al. | |
| 2009/0087317 A1* | 4/2009 | Keener | 416/224 |
| 2011/0155257 A1* | 6/2011 | Sundholm | 137/15.01 |

OTHER PUBLICATIONS

International Search Report and Written Opinion of the International Searching Authority issued in International Application No. PCT/US2012/031974 dated Jul. 6, 2012.

* cited by examiner

*Primary Examiner* — Sean E Conley
(74) *Attorney, Agent, or Firm* — Venable LLP; Jeffri A. Kaminski

(57) ABSTRACT

A system for ozone sterilization of waste material, includes a tank configured to receive waste material, ozonated water, and ozone gas. The system further includes a pump coupled to the tank to receive the waste material and the ozonated water from the tank and form a slurry. The pump includes a cutter assembly to reduce a particle size of the slurry through cutting. Additionally, the system includes a circulation loop coupled between the tank and the pump to receive the slurry from the pump and re-circulate the slurry to the tank until the slurry is sterilized. A method for ozone sterilization of waste material is also disclosed.

9 Claims, 17 Drawing Sheets

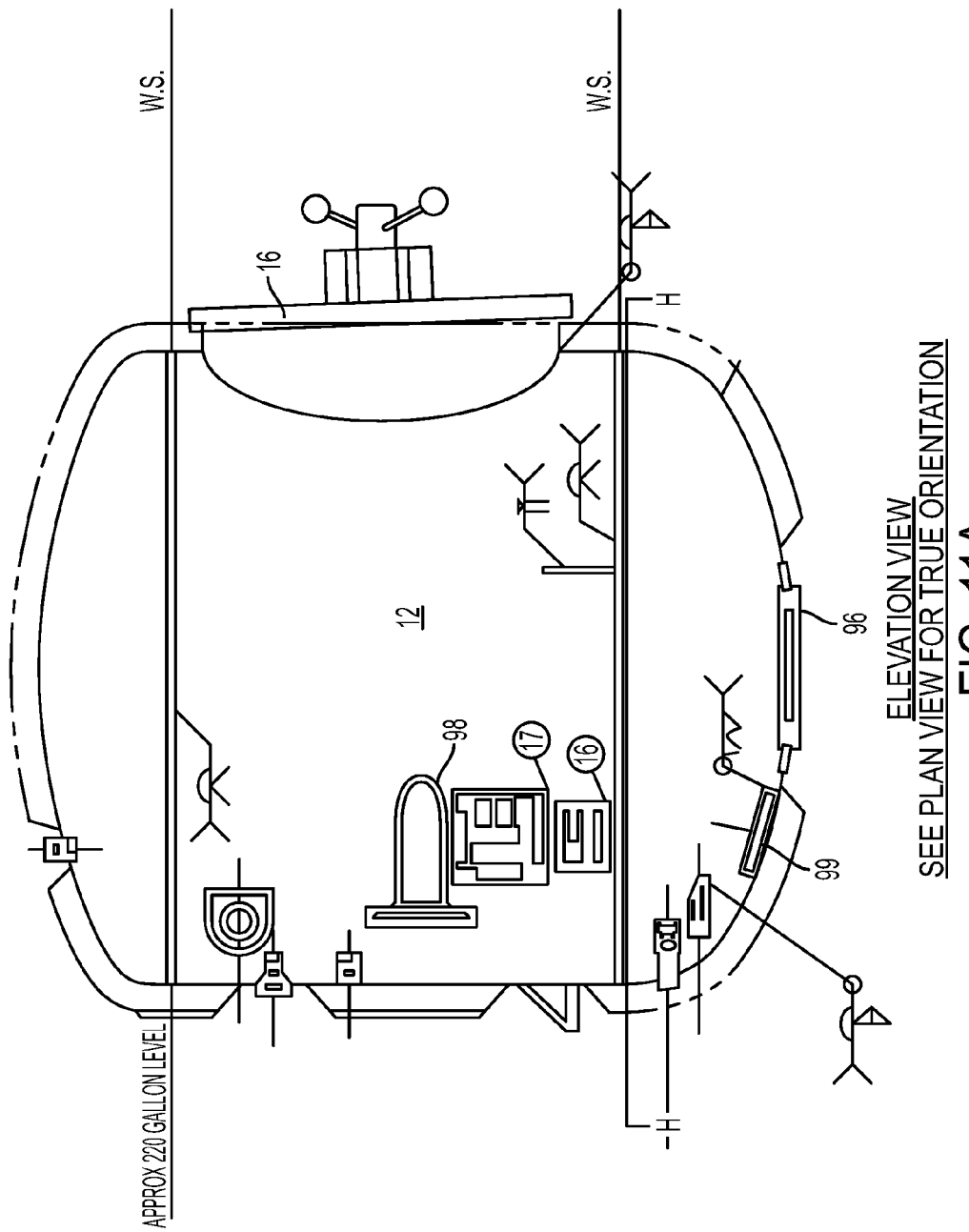

PLAN VIEW

BOTTOM HEAD VIEW
SECTION H-H

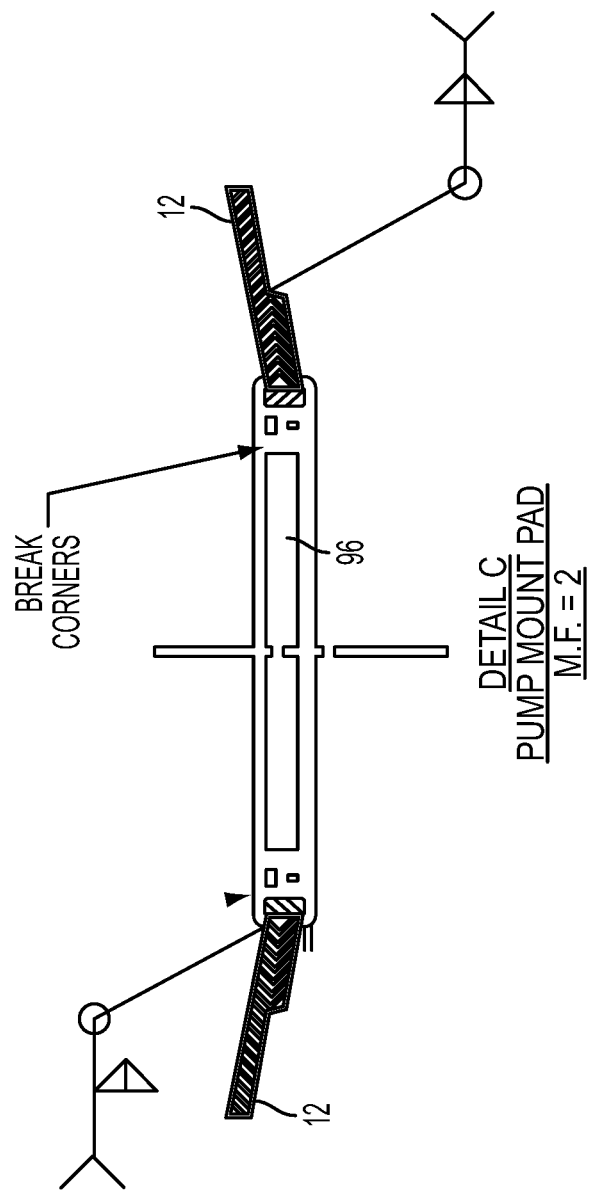

DETAIL F
WELDMENT
M.F. = 2

OSS PROCESSING
CONTROL STAGES

| | NAME | DESCRIPTION | RECOVER TO STAGE |
|---|---|---|---|
| 302 | INITIAL STAGE | INITIALIZE, OZONE GENERATOR | |
| 304 | SLEEP | KEEP UNIT LOCKED SO IT CANNOT BE STARTED | INITIAL STAGE |
| 306 | READY-TO-START | UNIT READY FOR PROCESS TANK DOOR TO BE CLOSED AND START BUTTON TO BE PUSHED | INITIAL STAGE |
| 308 | OZONATE | FILL PROCESS TANK WITH OZONE GAS | INITIAL STAGE |
| 310 | FILL | FILL PROCESS TANK WITH OZONATED WATER | OZONATE |
| 312 | GRIND | CHOP AND RECIRCULATE MATERIAL | FILL |
| 314 | STERILIZE | CALCULATE STERILIZATION TIME BASED ON O3 CONCENTRATION AND TIME AS MATERIAL CONTINUES TO BE CIRCULATED | GRIND |
| 316 | VENT | VENTING AIR FROM PROCESS TANK TO ATMOSPHERE | STERILIZE |
| 318 | DISCHARGE | DISCHARGE CONTENTS OF PROCESS TANK INTO SEPARATOR | VENTING |
| 320 | RINSE | RINSE PROCESS TANK WITH WATER FROM FACILITY | DISCHARGE |
| 322 | DRAIN | DRAIN PROCESS TANK AND SEPARATOR | RINSE |
| 324 | COMPLETE | PRINT REPORT AND STORE HISTORIES | DRAIN |

FIG. 13

SYSTEM AND METHOD FOR PROCESSING WASTE MATERIAL

CROSS-REFERENCE TO RELATED APPLICATIONS

The present application claims the benefit under 35 U.S.C. §119(e) of U.S. Provisional Patent Application No. 61/330,327, filed on May 1, 2010, the content of which is expressly incorporated herein by reference in its entirety.

BACKGROUND

1. Field of the Invention

The present invention relates generally to systems and methods for processing waste material, and more particularly to such systems and methods which may not only effect the sterilization and optionally, disinfection, of waste material such as medical (also known as "red bag"), food, disposable diapers, and other types of waste, but also reduce the volume of such waste material, and dispose of water soluble polymeric or fibrous waste material.

2. Statement of the Prior Art

Waste management evolved in the latter part of the twentieth century into an industry of considerable importance, as societal and environmental attention had focused on the conventional processes by which waste has to date been handled for disposal. These conventional waste disposal processes included incineration, dumping at sea, and burial in landfills. Each of these processes, however, is encumbered by significant societal and environmental disadvantages and regulatory restrictions.

Incineration is objectionable due to its attendant chemical and particulate pollution of the atmosphere and surrounding locales. Further, these pollutants can be transported over great distances by prevailing winds, thereby extending the scope of environmental impact beyond the immediate locale of the incinerator. Waste disposal in the oceans is objectionable due to its adverse environmental impact on sea life and coastal shores. Landfills are objectionable due to their attendant spatial demands, offensive odors, contamination of ground water and potential for production of hazardous substances arising from the mixing and interaction of buried materials.

Spatial considerations are especially prevalent in urban centers, where population growth has resulted in suburban expansion to locations well outside of the urban center, necessitating in some instances in the relocation of existing landfills and the creation of costly new landfills at locations geographically remote from the centers they serve. Disposable diapers, for example, have proven to be an increasing problem for municipal disposal.

Additional waste disposal problems arise in view of the type of waste that is to be disposed. For example, special precautions are required for the disposal of biological and medical waste due to the overwhelming concern for preventing the creation and/or spread of infectious disease. Further concerns arise due to the presence of extremely sharp medical instruments such as needles, knives, and broken glass containers that can cut or lacerate the skin of personnel and animals with which the waste comes in contact, thereby presenting both a risk of physical harm and biological contamination. For these reasons, such waste is typically thermally or chemically treated and buried in dedicated medical waste disposal facilities. The treatment should be of a type that renders the waste biologically neutral or inert.

Sterilization can typically be accomplished by any one of a variety of prescribed chemical and non-combustion thermal treatment regimens, as well as incineration or autoclaving. Autoclaving provides for exposure of the waste to heat at upwards of 250° F. (121° C.) at 15 pounds per square inch ("PSI") for 15-40 minutes. While sterilization can be accomplished in both dry air and steam environments, steam autoclaving is generally preferred due to its greater penetrating capabilities (especially important for sterilizing "soft" waste such as textiles and gauze) and its lethality via the process of denaturation. Longer periods are used to assure steam penetration of heavy, fluid-absorbable loads. Faster processing can be accomplished for some waste materials by increasing temperature and pressure. However, a significant disadvantage of steam autoclaving without reducing the size of the material is its failure to assure complete penetration of the waste and its exposure to the heat contained within the water vapor. Further disadvantages include the tendency for autoclaves (both steam and dry) to stratify and to trap comparatively cool air in pockets, thereby precluding sterilization. In addition, the waste is neither reduced in volume or in mass; instead, mass can increase in some instances (i.e., textiles and gauze) due to the absorption of water vapor, thereby exacerbating the problem of waste disposal referenced above.

A popular alternative to autoclaving is chemical disinfection. Chemical sterilization generally provides for exposure of the waste material to an antiseptic solution such as liquid chlorine for a prescribed time interval; however, the use of chemical sterilizing agents presents disposal problems for the liquid following waste treatment due to the toxicity of chlorine and other antiseptic solutions.

In view of the foregoing, there is a pressing societal need to not only reduce the volume of waste material that is produced, but also to more effectively and efficiently process the waste so that it has a diminished environmental impact. This need is especially pressing in instances where waste is produced in bulk, as can occur in hospitals, clinical laboratories, research facilities, nursing homes, restaurants, and the like.

While efforts are being undertaken to reduce waste production, these efforts alone will not eliminate the various problems associated with waste disposal, particularly in the medical and dental industries, where single patient use (i.e., non-reusable) surgical instruments have gained widespread acceptance due to concerns over spread of the family of hepatitis viruses and HIV.

Moreover, it would be preferable to provide systems and methods for processing waste material at a lower cost, environmentally and economically.

SUMMARY

Accordingly, it is an object of the present invention to provide a system and method for sterilizing medical and other forms of waste. Another object of the invention, when waste is in a bulk form, may be to reduce the volume of waste solids for disposal. It is a further object of the present invention to provide a system and method for treating water-soluble polymeric or fibrous waste material.

According to one embodiment, a waste disposal system and/or method is directed to optimally sterilizing waste and to reducing the volume of waste solids, thereby simplifying procedures for waste disposal and reducing the demand for disposal space in landfills. While embodiments of the present invention may be particularly advantageous for use in processing bulk medical waste in the form of aggregate or "red-bagged" medical waste along with non-aggregate medical waste, its principles may be equally applicable for the treatment of other forms of waste including contaminated liquid waste and items such as food waste produced incident to the operation of restaurants and so-called "fast food" establishments.

According to another embodiment, the system and/or method can also be used for processing disposable diapers. In this latter regard, waste treatment in accordance with the teachings herein greatly reduces the organic content of the waste solids, thereby resulting in a diminution of rodent and other pest infestation typically associated with food waste disposal as well as the capacity requirements for waste receptacles (i.e., "dumpsters") on-site at the restaurant. Alternatively, the principles of the invention may be applied to the disposal of water soluble polymeric or fibrous waste materials, whereby treatment results in the dissolution of the waste material.

According to a further embodiment, a closed waste processing system may be provided that is operable to effect biological neutralization of waste by a process of waste sterilization. An ozone system can optionally be provided that is operable through appropriate valve apparatus to deliver ozone gas, ozonated water and/or other suitable ozonated and/or disinfecting fluids to a process tank, also known as a decontamination chamber, to mix with the waste material as it is drawn toward a cartridge/cartridge/macerator pump, also known as a waste processing chopper/pump assembly, positioned downstream from the process tank. Alternatively, the ozonated water may be produced directly within the process tank, where the water and/or fluid can be supplied from a supply line such as a hot or cold water line and the ozone can be supplied from an ozone generator. In one embodiment, the ozonated fluid is water. However, the principles of the present invention are applicable for other liquids.

According to one embodiment, output from the pump may be directed to the process tank and may circulate therethrough in a closed circuit in a continuous manner, during which time the waste solids are ground by the cartridge/cartridge/macerator pump to successively finer particles and mixed with the circulating ozonated fluid in the processing tank.

According to another embodiment, the waste and fluid mixture may be oxygenated to an ozone concentration range 5-50% and a temperature of about 85° F. to about 165° F. within the process tank and directed to a high-capacity cartridge/cartridge/macerator pump, which may grind the waste to further reduce its volume and return the fluid and entrained ground waste to the process tank for continued processing. The fluid and entrained waste may be continuously processed and circulated by the cartridge/cartridge/macerator pump and oxygenated to the requisite processing concentration within a closed loop that extends from the process tank to the cartridge/cartridge/macerator pump and back to the process tank for a prescribed time interval to ensure processing to a desired level of biological neutralization.

According to another embodiment, operation of the system may be monitored by various sensors having a suitable output to appropriate control apparatus to ensure processing of the waste in a fail-safe manner. A record can optionally be rendered which details operation of the system as a function of time, concentration and temperature. Processed waste can optionally be filtered to separate solids in excess of prescribed dimension to permit for drying of the solids by suitable dehydration apparatus. Processed waste solids can optionally be compacted by suitable compacting apparatus to further reduce waste volume. The mixture of processing fluid and liquid waste can be passed into a sanitary sewer for disposal to meet municipal requirements. In a further embodiment, a portion of the processing fluid and liquid waste may be collected following processing and returned to the decontamination chamber prior to cooling for use in processing of another waste processing cycle, thereby further reducing waste production and energy requirements for the waste processing system.

BRIEF DESCRIPTION OF THE DRAWINGS

These and other objects and advantages of the present invention will become apparent from the following specification when read in conjunction with the accompanying drawings, wherein like reference numerals/characters represent like or corresponding parts throughout the various views:

FIGS. 11A-11E depict various views of connections to the process tank, according to an embodiment of the present invention;

FIG. 13 is a chart showing various control stages of the ozone sterilization system, according to an embodiment of the present invention.

DETAILED DESCRIPTION

Figure 1:
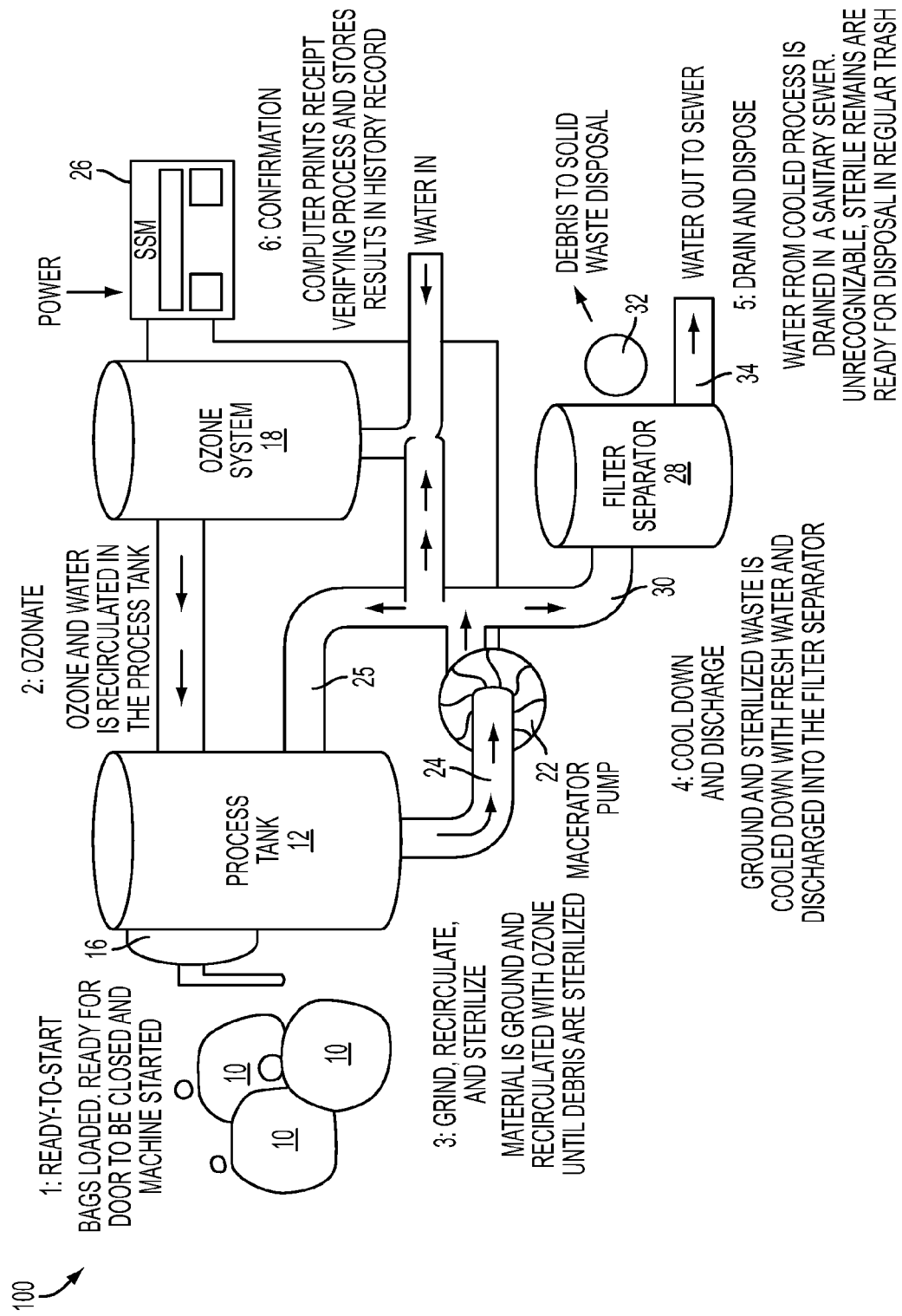
FIG. 1 is a system diagram of the ozone sterilization system, in accordance with an embodiment of the present invention.

The various embodiments of the invention are discussed in detail below. While specific embodiments are discussed, it should be understood that this is done for illustration purposes only. In describing and illustrating the embodiments, specific terminology is employed for the sake of clarity. The embodiments so disclosed, however, are not intended to be limited to the specific terminology selected. Persons of ordinary skill in the relevant and related art will recognize that other components and configurations may be used without departing from the true spirit and scope of the embodiments. It is to be understood that each specific element includes all technical equivalents that operate in a similar manner to accomplish a similar purpose. Therefore, the examples and embodiments described herein are non-limiting examples.

Generally, the term "disinfection" and its variants pertains to the destruction of pathogenic microorganisms or their toxins or vectors. The term "sterilization" and its variations pertains to the destruction of all living microorganisms and their spores, thereby rendering the material so processed void of all living matter. For the purposes of this application, the term "maceration" refers to cutting up and shredding waste material while the waste material is immersed in an ozonated liquid.

Ozone is a chemically active radical species of oxygen, commonly produced by ionization of either air or pure oxygen. Ozone includes disinfecting properties, and may be used as a sterilizing agent in certain applications. Ozone is considered very safe as evidenced by the approval of the U.S. Food and Drug Administration for use in treating food products. Unlike conventional disinfecting chemicals, ozone does not form hazardous disinfectant by-products that are harmful to the environment or are toxic to animals and humans. Once ozone has fully reacted with substances in water or air, excess gas decomposes quickly to normal oxygen and is reabsorbed into the atmosphere. Commercial ozone generators are readily available, and economically produce significant amounts of ozone.

Systems and methods of processing waste material in accordance with the various embodiments of the present invention, as described below, may be comprised in a similar manner as those shown and described in U.S. Pat. No. 5,277,869 (Glazer et al.), U.S. Pat. No. 5,427,737 (Glazer et al.), and U.S. Pat. No. 5,582,793 (Glazer et al.). However, it has been found that by using ozone in the manner shown and described herein below, hot water, steam, and boiler components may be eliminated. This not only reduces the overall cost of manufacturing such systems, but also reduces the amount of water and electricity used in the process and, thereby reduces the operating costs. Other benefits of the present invention include the discontinuance of needing an ASME-certified tank, thereby avoiding altogether the complexity and expense associated with the construction of ASME-certified, pressurized systems; elimination of other unnecessary components as a result of removing the hot water, steam, and boiler components; greater capacity due to short cycle times; and a smaller footprint not only makes it easier to manufacture and lighter to transport, but also enables a portable embodiment of systems according to the present invention.

With reference now to the drawings, FIG. 1 depicts a system diagram of the ozone sterilization system (OSS) 100 in accordance with an embodiment of the present invention. In FIG. 1, regulated medical waste (RMW) 10, bagged or otherwise contained and sealed, may be placed within a process tank 12 for sterilization. Such waste can be in the form of virtually any type of non-toxic inorganic or organic material, such as medical waste, food waste, rubber, plastics, and the like for which it is desirable to disinfect, or optimally render biologically neutral (i.e., biologically inert or devoid of living organisms) via sterilization. Medical waste can include, by way of non-limiting example, sharps such as needles, knives and blades, trocars, clamps, glass containers, gauze and bandages, surgical gloves and gowns, and various other instruments and paraphernalia which contacts internal body fluids such as blood, lymphatic, semen, and vaginal fluids. It may also include sharps containers containing such waste. Medical waste can also include, for example, small research animals, animal bedding, plastic animal cages, animal and human pathological waste and egg embryos. Waste sterilization is preferred in instances such as with some forms of medical waste where bacteria, viruses and/or spores may be present, in which case all living organisms associated with the waste must be destroyed prior to its disposal.

The amount of RMW 10 placed within the process tank 12 should be of an appropriate size, for example, between 75 and 200 pounds of waste. Once loaded, the door gasket 14 (See FIG. 2) of the process tank 12 may be wiped clean and the door 16 of the process tank 12 may be closed and secured.

An ozone system 18 may be connected to the process tank 12 via supply line 20. The ozone system 18 may inject ozonated water, as well as ozone gas, into the process tank 12 to mix with the RMW 10. The ozonated water may be produced from hot or cold water tap water. The combination of the ozonated water and RMW 10 is referred to as "slurry."

Ozone is about 13 times more soluble than oxygen in water at standard temperature and pressure. It is readily decomposed back to oxygen, from which it is formed. This decomposition is very rapid in the presence of ozone demanding impurities, i.e., in water, but is slower in high purity water or in the gaseous phase. Turbulence or churning of ozonated water by, for example, a pump, may further cause the ozone to decompose back into oxygen. Therefore, in order to compensate for the decomposition of the ozonated water in the process tank 12, the ozone system 18 may deliver additional ozone gas into process tank 12 throughout the duration of the sterilization process to maintain a particular concentration of ozone in the slurry. As discussed below, a sensor may monitor the ozone concentration of the slurry.

Ozone is produced from dried air or from oxygen. The conversion of oxygen into ozone requires the rupture of the very stable bond of the oxygen molecule. This is accomplished commercially by passing a clean dry, oxygen-containing gas through an electrical discharge. In this method, high voltage is applied across a discharge gap and collisions occur between electrons and oxygen molecules. A fraction of these electrons have sufficient kinetic energy (around 6 or 7 eV) to dissociate the oxygen molecule to form ozone, while the remaining electrons release their energy as heat.

Ozone generators may be assembled with modular electrodes and electronics; reducing the number and cost of spare parts. The ozone generators may be fully assembled and factory tested. They may include mechanical, electrical and instrument fittings. According to one embodiment, the ozone system 18 may be a "corona discharge" generator, whereby lined glass or ceramic dielectric tubes, are fitted inside water cooled stainless steel tubes and provided with a gap, "discharge gap", between the two surfaces. Gas may be passed through the annulus (discharge gap) and a high voltage passed across the gap through the gas results in ozone generation. According to another embodiment, the ozone system 18 may be a MCP series ozone generator. The MCP series is a new line of high technology ozone generators that are compact, inexpensive and easy to use.

According to a further embodiment, the ozonated water and gas may be produced directly within the process tank 12. In this embodiment, water and/or another suitable fluid may be supplied from a supply line such as a hot or cold water line and the ozone gas may be supplied directly by an ozone generator into the process tank 12. The water and ozone gas may mix within the process tank 12 to produce ozonated water having a particular concentration.

In one embodiment, approximately 60 gallons of ozonated water may be injected from the ozone system 18 into the process tank 12. The ozonated water from the ozone system 18 may mix with the RMW 10 placed within the process tank 12 for a pre-determined duration of time.

According to one embodiment, the OSS 100 may also be particularly useful for effecting sterilization of virtually all forms of non-toxic waste by exposing the waste to, for example, water ozonated to an ozone concentration range of approximately 5-50% and heated to a temperature of about 85° F. to about 165° F. within the process tank 12. The ozonated water may be produced from standard hot tap water.

According to another embodiment, sterilization may be implemented by elevating percentage of ozone concentration in the liquid mixture to about 20% and maintaining that concentration for a time interval of about eight minutes. A dissolved ozone analyzer and ambient ozone analyzer may be provided to monitor the ozone concentration. Temperature sensors may be provided along the fluid flow path to provide an indication of circulated fluid temperature throughout system operation and to ensure that the requisite processing temperature has been maintained for the required time interval.

A maceration (chopper) pump 22 may be connected to the process tank 12 via pipe 24. The cartridge/cartridge/macerator pump 22 may be generally comprised of a cutter assembly and a pump assembly (See FIG. 7 for details). The cartridge/macerator pump 22 may include multiple cutting surfaces to separate and reduce the size of the RMW 10 into smaller particles while the RMW 10 remains completely exposed to the ozonated water in the slurry.

The cartridge/macerator pump 22 may continuously recirculate the slurry through a circulation loop 25 back into the process tank 12 and back through the multiple cutting surfaces of the cartridge/macerator pump 22 until the RMW debris particles are of a sufficiently small size and the proper ozone saturation and duration of sterilization treatment is complete. The term "continuously" refers to the cycling of the slurry between the process tank 12 and the cartridge/macerator pump 22 until the slurry is sterilized. There may, however, be intermittent pauses or gaps in the cycling, as long as the overall goal of sterilization is achieved.

According to one embodiment, appropriate size of the RMW particles may be determined by the amperage of the 15 HP chopper pump and the amount of time the cycle has been operating. According to one embodiment, the RMW particles may have a size in the range of about 1/16 in. (1.5 mm) to about 1/4 in. (6.5 mm) in their largest dimension.

In another embodiment, the cartridge/macerator pump 22 may be slowed before the ozonated water is introduced into the process tank 12. The ozonated water may be mixed in a closed circuit with the RMW 10, and allowed to react for a predetermined period of time. For example, while this time may be about 6 minutes for typical batches of about 80 pounds of waste to from 75 to about 100 gallons of water, this time may be varied as a function of the temperature of the slurry and concentration of ozone used. Such water may be cold or hot water in a temperature range of about 85° F. to about 165° F. The concentration of ozone in the ozonated water may be from about 5% to about 50%.

According to another embodiment, once the waste material has been ground by the pump and exposed to ozone for the prescribed period of time, the water and entrained waste particulate may be checked for ozone concentration so as to permit for disposal of the liquid portion of the mixture into the municipal waste disposal system. For example, an operating system 26, including residual and ambient analyzers, may monitor the sterilized waste material to see that any remaining ozone has been reduced to oxygen prior to discharge of the waste from the process tank 12.

Once properly sterilized, may be discharged via pipe 30 to a filter separator 28. The filter separator 28 may filter or separate the solids from the liquids of the sterilized waste. The entrained waste solids may be filtered from the processed waste, compacted and disposed of in a conventional manner, whereas the waste liquids may be passed into the municipal sewer lines. As shown in FIG. 1, waste solids may be captured by a filtering device 32, while waste liquid may be discharged into the sanitary sewer system via pipe 34. The waste solids may then be disposed of as ordinary solid waste via a municipal trash compactor.

According to one embodiment, the processed waste may be filtered to separate solids in excess of a prescribed dimension to permit for drying of the solids by a suitable dehydration or drying apparatus. According to another embodiment, processed waste solids may be compacted by suitable compacting apparatus to further reduce waste volume.

Waste processing in the foregoing manner may be programmatically controlled in accordance with an operating system 26 or a pre-established system program. Variables such as pump speed, fluid flow rate, slurry ozone concentration, ozonated water temperature, and duration of operation may be selected within prescribed ranges in accordance with such factors as the nature and quantity of waste to be treated, and the concentration of ozone mixed in solution therewith. Further parameters which affect waste processing may include the dimensions of the conduits through which processed material and fluid flow. The foregoing variables and parameters may be selected to provide for the production of processed waste solids of a size in the range of from about 1/16 in. (1.5 mm) to about 1/4 in. (6.5 mm) in their largest dimension.

A printout of system operation parameters such as ozone concentration, exposure time and waste temperature throughout the processing procedure may optionally be provided to render a permanent record of system operation. Likewise, at the end of every sterilization cycle, a detailed sterilization report may be electronically printed by the operating system 26 illustrating, for example, the date, batch, time of start and finish of cycle. Alternatively, or in conjunction with printer operation, the various above-referenced operation various parameters may be stored in electronic memory for subsequent recall and display on a visually perceptible device such as a cathode ray tube (CRT) or similar display of alphanumeric and graphic data. In all instances, however, the waste processing proceeds for a period of time which provides for grinding and exposure of the waste to a circulating stream of ozonated water for a period of time that meets or exceeds the applicable standards and regulations governing material disinfection and sterilization in accordance with the selected form of waste treatment.

According to another embodiment, a housing 54 (See FIG. 4) may optionally be provided to enclose the OSS 100 and provide acoustic dampening.

Figure 2:
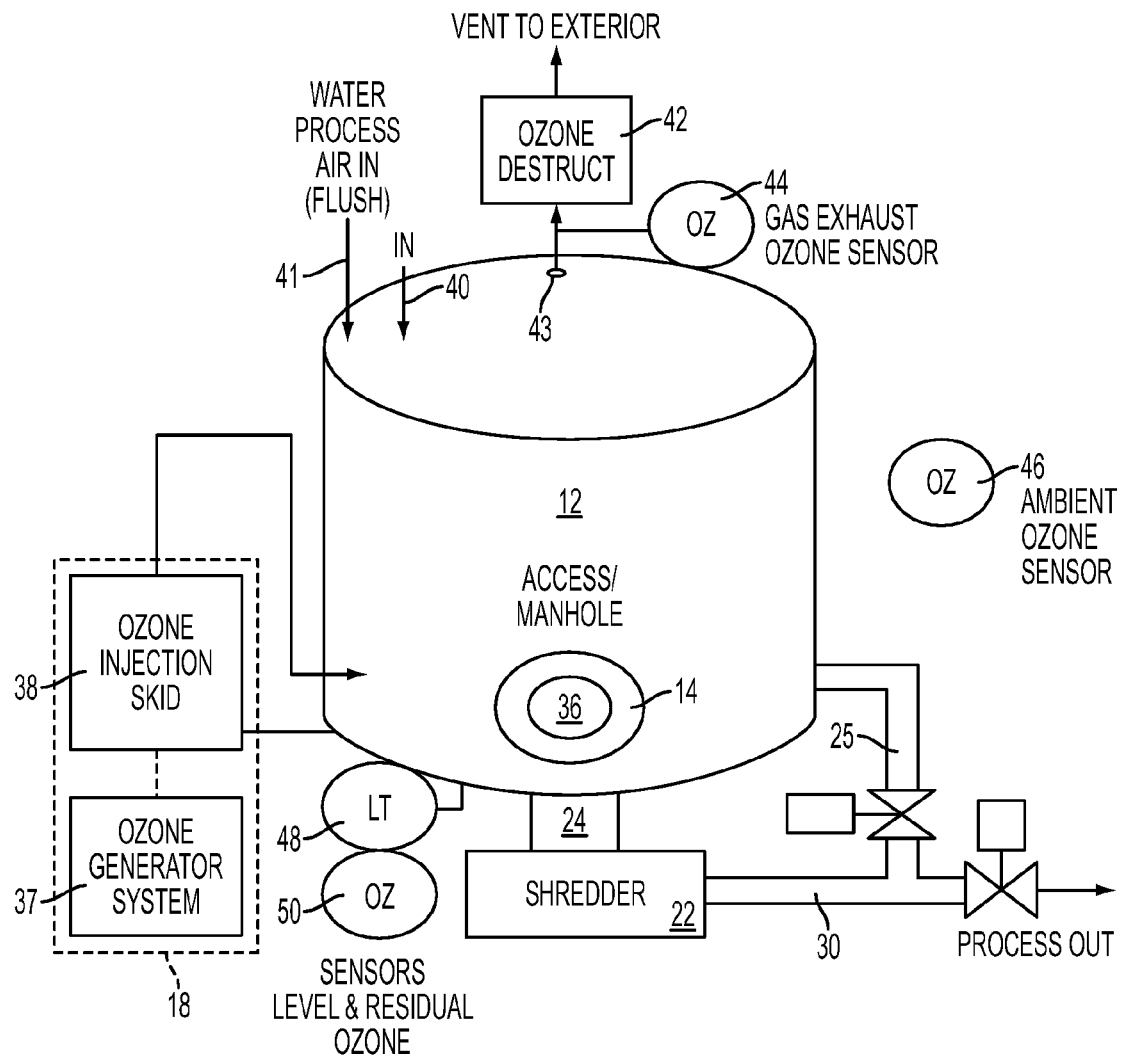
FIG. 2 is a perspective view of the process tank of the ozone sterilization system, in accordance with an embodiment of the present invention.

FIG. 2 is a perspective view of the process tank 12 of the OSS 100 in accordance with an embodiment of the present invention. The process tank 12 may include an access hole 36, having a lip (not shown) and an interior gasket 14, to be covered by door 16 during the ozonation and sterilization cycles.

The ozone system 18, in the embodiment of FIG. 2, may include an ozone generator 37 and an ozone injection skid 38. The ozone generator 37 may generate ozone gas, for example, in the manner described above. The ozone injection skid 38 may connect to the process tank 12 to "inject" ozonated water and/or ozone gas from the ozone generator 37 into the process tank 12.

The process tank 12 may include a water feed 40 and an air feed 41 to "flush" or clean the process tank 12 with air and/or water after the sterilization cycle is complete.

Additionally, the process tank 12 may include an air vent 43 to exhaust gas from the tank after use. A gas exhaust ozone sensor 44 may be connected to the air vent 43 to monitor the ozone concentration of the exhausted gas. If ozone levels are too high for release into the ambient air, an ozone destruct 42, connected to air vent 43, may filter the air through a charcoal filtering system to remove the excess ozone before exhausting the air into the ambient.

Ozone is a sharp irritant, and prolonged breathing of concentrations in excess of 1 ppmv should be avoided. The sharp odor of ozone is an indication of its presence. Ozone may be readily detected at concentrations of 0.1 ppmv or less (0.01 to 0.04 ppmv is the recognized odor detection threshold). The nose, however rapidly loses its ability to smell ozone. Odor alone should not be used as a warning of high ozone concentrations. Therefore, as shown in FIG. 2, an ambient ozone sensor 46 may be positioned in close proximity to the process tank 12 to detect and monitor the amount of ozone in the ambient air. This may serve as a safety feature to protect nearby users of the OSS 100.

Regarding the safety of ozone, gaseous ozone undergoes a thermal decomposition to oxygen at ordinary temperatures. This effect is accelerated by increases in temperature. For example, at 100° C., the half life of 5 wt. % ozone is 1.4 hours; at 300° C. the half life is 0.01 second. Commercial thermal ozone destruct units expose ozone to 350° C. for 4-5 sec. Mechanical interaction with solutions of ozone, e.g., those useful in accordance with embodiments of the present invention, will also decompose to oxygen. Further information may be found in a very comprehensive document prepared by the Compressed Gas Association, CGA P-34, Safe Handling of Ozone-containing Mixtures Including the Installation and Operation of Ozone-Generation Equipment. This document is available from the CGA at www.cganet.com.

Tank temperature and ozone sensors 48, 50 may be provided to monitor the temperature and ozone concentration levels of the slurry within process tank 12. If the ozone concentration level of the slurry is low, the operating system 26 may signal the ozone system 18 to inject additional ozone gas into the process tank 12.

Figure 3:
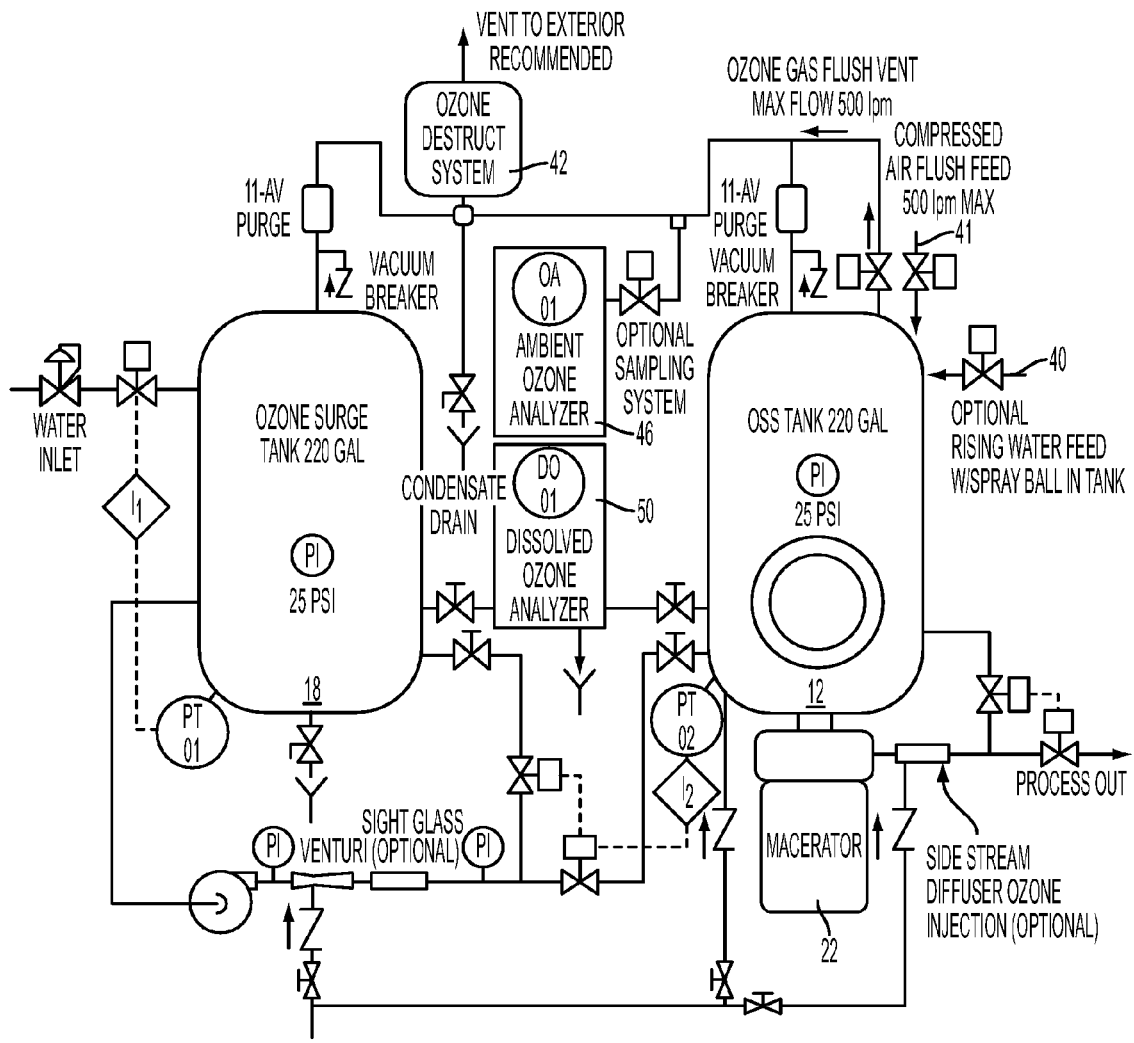
FIG. 3 is a system diagram of the process tank and the ozone system of the ozone sterilization system, in accordance with an embodiment of the present invention.

FIG. 3 is a system diagram of the process tank and the ozone system of the ozone sterilization system in accordance with an embodiment of the present invention and further exemplifies the features described above.

Figure 4:
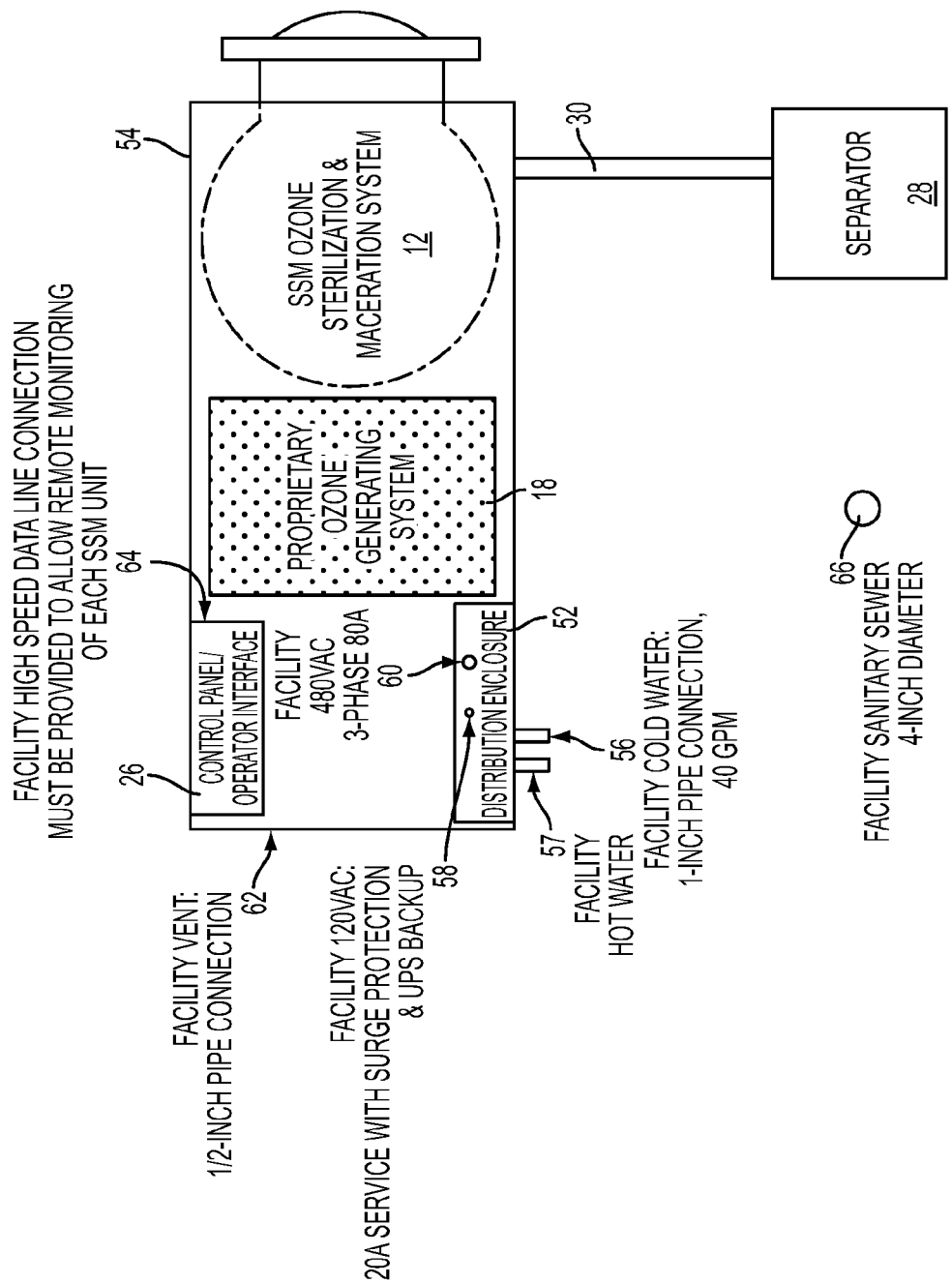
FIG. 4 is a schematic diagram showing the size and set up of the ozone sterilization system, in accordance with an embodiment of the present invention.
Figure 5A:
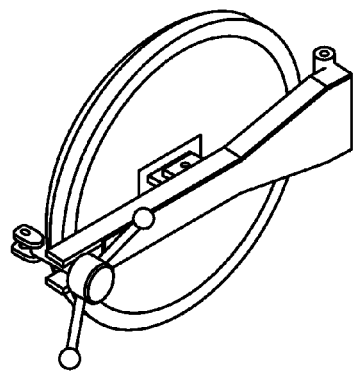
FIGS. 5A-5E depict various perspective views of the door of the process tank of the ozone sterilization system, according to one embodiment of the invention.
Figure 5B:
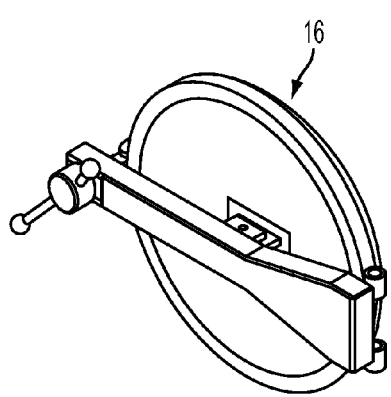
Figure 5C:
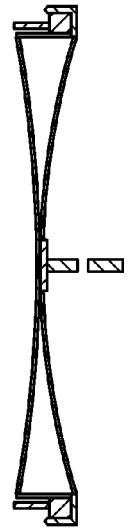
Figure 5D:
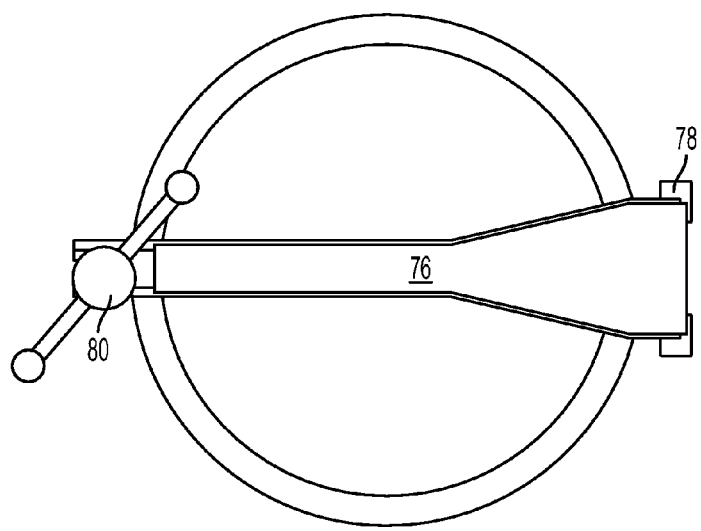
Figure 5E:
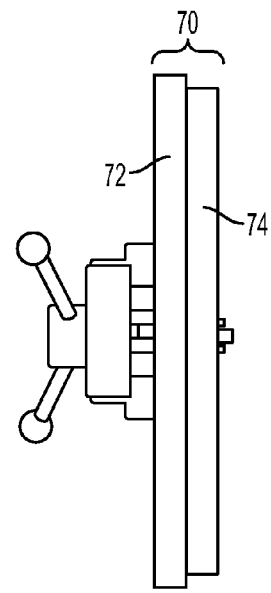

FIG. 4 is a schematic diagram showing the size and set up of the ozone sterilization system 100 in accordance with a different embodiment of the present invention. According to one embodiment, the OSS 100 may fit within a 46" by 116" rectangular foot print, with an external filter separator 28. Thus, the OSS 100 is compact and easily adapted to be placed in pre-existing building spaces.

The embodiment of FIG. 4 also shows a distribution enclosure 52 positioned within an overall housing 54 of the OSS 100. The distribution enclosure 52 includes a facility 120 Volt AC connection 58, and a facility 480 Volt AC connection 60. The facility cold water connection 56 that connects into housing 54 may supply, for example, water into the OSS 100 at approximately 40 gallons per minute and may be a 1-inch pipe connection. The facility hot water connection 57 that connects into housing 54 may supply, for example, water into the OSS 100 at approximately 10 gallons per minute at a temperature of approximately 120° F. to approximately 150° F. The facility hot water connection 57 may be a ¾ inch pipe connection and may supply approximately 70 gallons of water into the OSS 100 two times per hour. The pressure requirements for both the facility cold and hot water connections 56, 57 may be between about 40 psi to about 60 psi. The facility 120 Volt AC connection 58 may, for example, be a 20 Amp service with surge protection and UPS backup. The facility 480 Volt AC connection 60 may, for example, be a three-phase 80 Amp service. The housing 54 of the OSS 100 may further include a facility vent 62 having, for example, a half inch pipe connection.

According to the embodiment shown in FIG. 4, the operating system 26, also referred to as the "Control Panel/Operating Interface," may include a facility high speed data line connection 64 to allow remote monitoring of each OSS 100 unit in the facility. FIG. 4 shows the location and proximity of a facility sanitary sewer line 66 from the filter separator 28. The facility sanitary sewer line 66 may have, for example, a four-inch diameter.

FIG. 5A-5F show various views of the door 16 of the process tank 12 of the ozone sterilization system 100 according to one embodiment of the invention. The door 16 includes a door body 70 having an exterior plate 72 of sufficient size to securely cover the outside of the access hole 36 (See FIG. 2) and a smaller interior plate 74 adapted to engage the gasket 14 of the access hole 36 to preserve an air-tight seal of the process tank 12 while the door 16 is closed during sterilization. As shown in the cross-sectional view of FIG. 5C, the door body 70 of the door 16 may be concave to provide a greater resistance to the pressure within the process tank 12. The curvature of the door body 70 allows the door 16 to withstand greater pressure per square inch.

The door 16 further includes a structural lever 76 that is connected to and spans across the width of the exterior plate 72 and is hingedly attached via a hinge device 78 to the exterior housing of the process tank 12. On an opposite side of the hinge device 78, the structural lever 76 connects to a door latch 80 that may be twisted or turned to tighten the door 16 in an air-tight seal. Additionally, the operating system 26 may include a door sensor (not shown) to alert a user if the door is open or unlocked.

According to one embodiment, the access hole 36 and the door 16 are substantially circular in shape. Other shapes may be used as well. According to another embodiment, the access hole 36 of the process tank 12 may be sufficiently sized to receive at least one 32 to 34 gallon-sized bag of RMW 10. For example, an interior diameter of the access hole 36 may be approximately 24 inches. The access hole 36 may further be sufficiently positioned to allow an operator to easily place the RMW 10 into the process tank 12.

Figure 6:
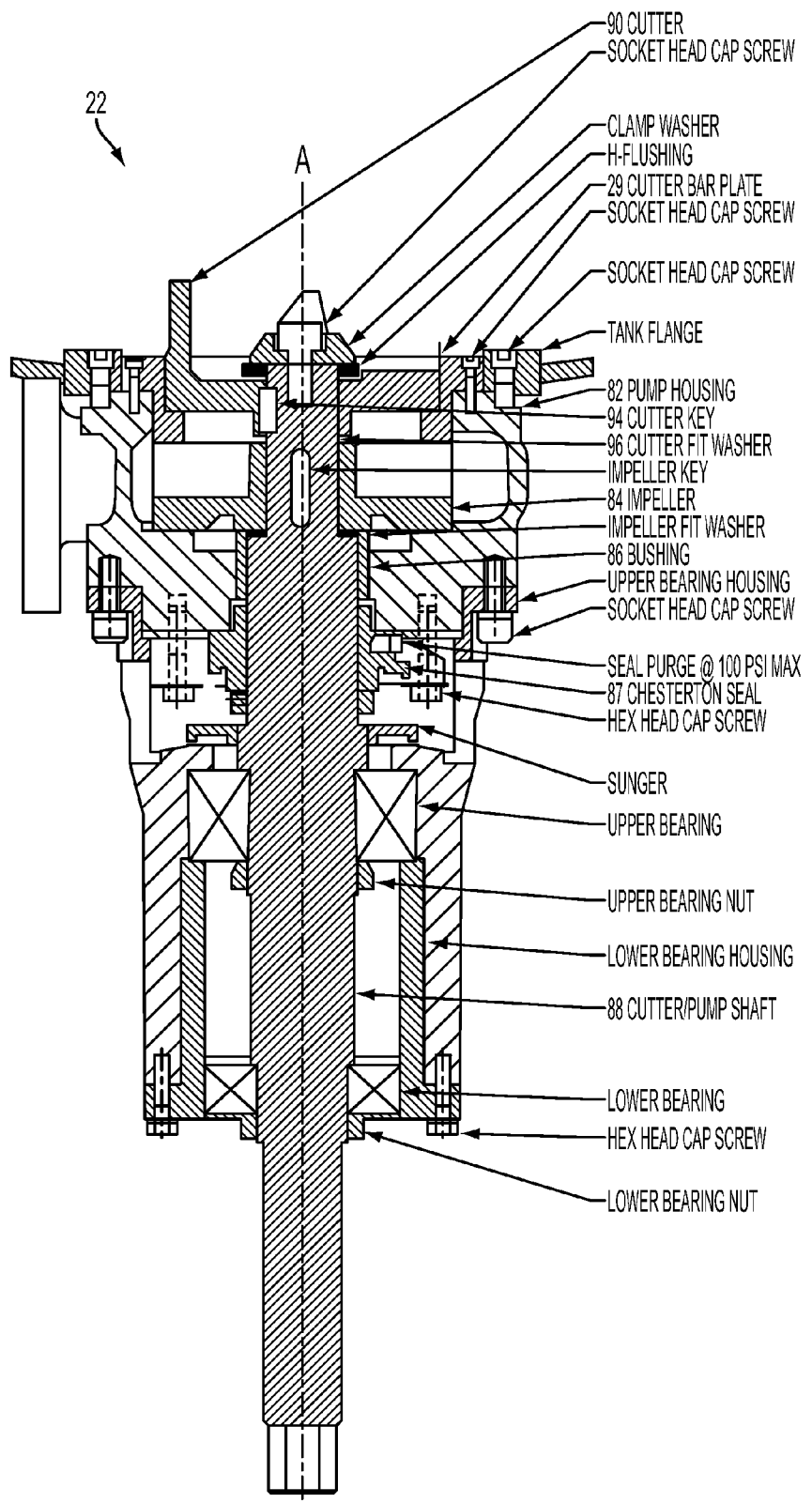
FIG. 6 is a cross-sectional view of the cartridge/cartridge/macerator pump of the ozone sterilization system, according to an embodiment of the present invention.

FIG. 6 is a cross-sectional view of the cartridge/cartridge/macerator pump 22 of the ozone sterilization system 100 according to an embodiment of the present invention. The cartridge/cartridge/macerator pump 22 includes a cutter/pump shaft 88 aligned along an axis A and a surrounding pump housing 82. The cartridge/cartridge/macerator pump 22 may function as both a pump assembly and a cutter/chopper assembly. The pump assembly of cartridge/cartridge/macerator pump 22 may include an impeller 84 and a bushing 86 driven by the cutter/pump shaft 88. The cartridge/macerator pump 22 may further include a seal 87, for example, but not limited to a Chesterton seal. The cutting/chopping assembly of cartridge/macerator pump 22 may include a cutter 90, a cutter bar plate 92, a cutter key 94 and a cutter fit washer 96, also driven by the cutter/pump shaft 88, to reduce the size of the RMW 10 particles.

As shown below (See FIGS. 11A-11E), the cartridge/macerator pump 22 is positioned beneath the bottom of process tank 12. The slurry may be drawn into the pump 22 via impeller 84. The slurry may be first chopped by cutter 90, which may be a single-blade assembly that rotates within the process tank 12. The slurry may then be further reduced in size by the cutter bar plate 92, which may be a circular disk that includes a plurality of cutting surfaces positioned along an inside perimeter surface. The cutter bar plate 92 may be positioned between cutter 90 and impeller 84. This stacked configuration is known as a "cartridge system." The impeller 84 itself may include a plurality of cutting surfaces that may further reduce the size of the slurry particles. Once, the slurry has passed through the cutter 90, the cutter bar plate 92 and the impeller 84, it may be re-circulated back into process tank 12 for additional ozonation and chopping.

Figure 7A:
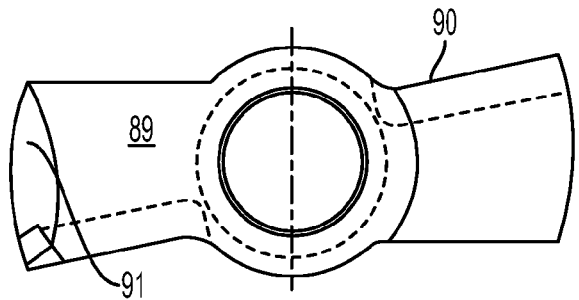
FIGS. 7A-7C are various views of the cutter of the cartridge/cartridge/macerator pump of the ozone sterilization system, according to an embodiment of the present invention.
Figure 7B:
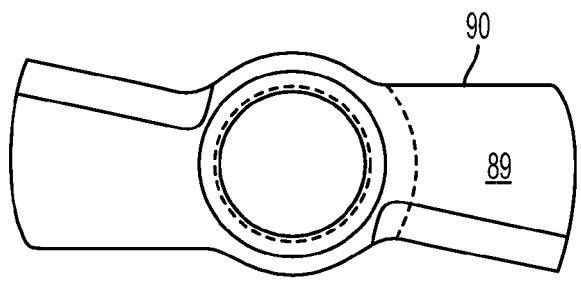
Figure 7C:
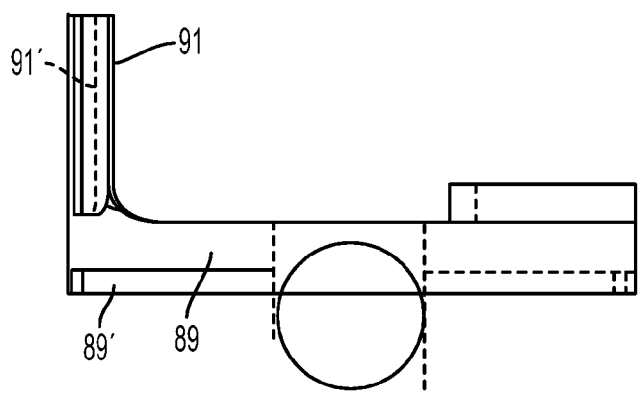
Figure 8A:
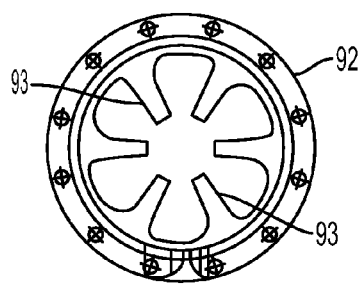
FIGS. 8A-8D are various views of the cutter bar plate of the mascerator pump of the ozone sterilization system, according to an embodiment of the present invention.
Figure 8B:
Figure 8C:
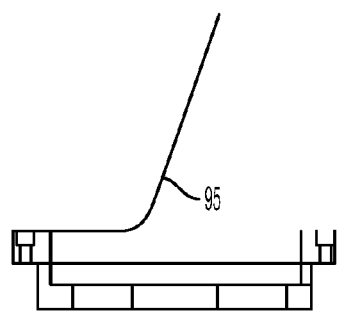
Figure 8D:
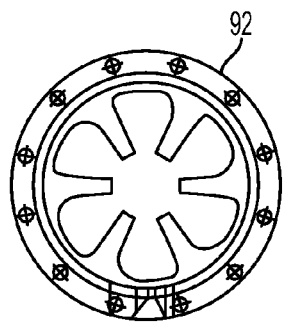

FIGS. 7A-7C are various views of the cutter 90 of the cartridge/macerator pump 22 of the ozone sterilization system 100, according to an embodiment of the present invention. The cutter 90 may include a base portion 89 and a blade portion 91 that projects upwards into the process tank 12 at a substantially perpendicular angle at one end of the base portion 89. The base portion 89 may span horizontally across and parallel above the impeller 84. The base portion 89 may include a carbon insert 89' along a bottom edge. The carbon insert 89' may be positioned beneath blade portion 91 to provide extra strength and durability during maceration. The blade portion 91 may also include a carbon insert 91', which may provide extra strength and durability of the blade portion 91 during cutting, such as chopping, of the slurry. According to one embodiment, the cutter 90 may made of a brazed carbide material. According to another embodiment, the cutter 90 may be a double-sail cutter.

FIGS. 8A-8D are various detailed views of the cutter bar plate 92 of the cartridge/macerator pump 22 of the ozone sterilization system 100, according to an embodiment of the invention. The cutter bar plate 92 may be a circular plate having a substantially hollow center. The interior portions of the cutter bar plate 92 may include a plurality of cutting surfaces 93. As the slurry is drawn through the hollow center of the rotating cutter bar plate 92 during maceration, the cutting surfaces 93 contact and further reduce the size of the slurry particles. Additionally, the cutter bar plate 92 may include a projection 95 that may be used to dislodge waste debris that become stuck above in the cutter 90.

Figure 9:
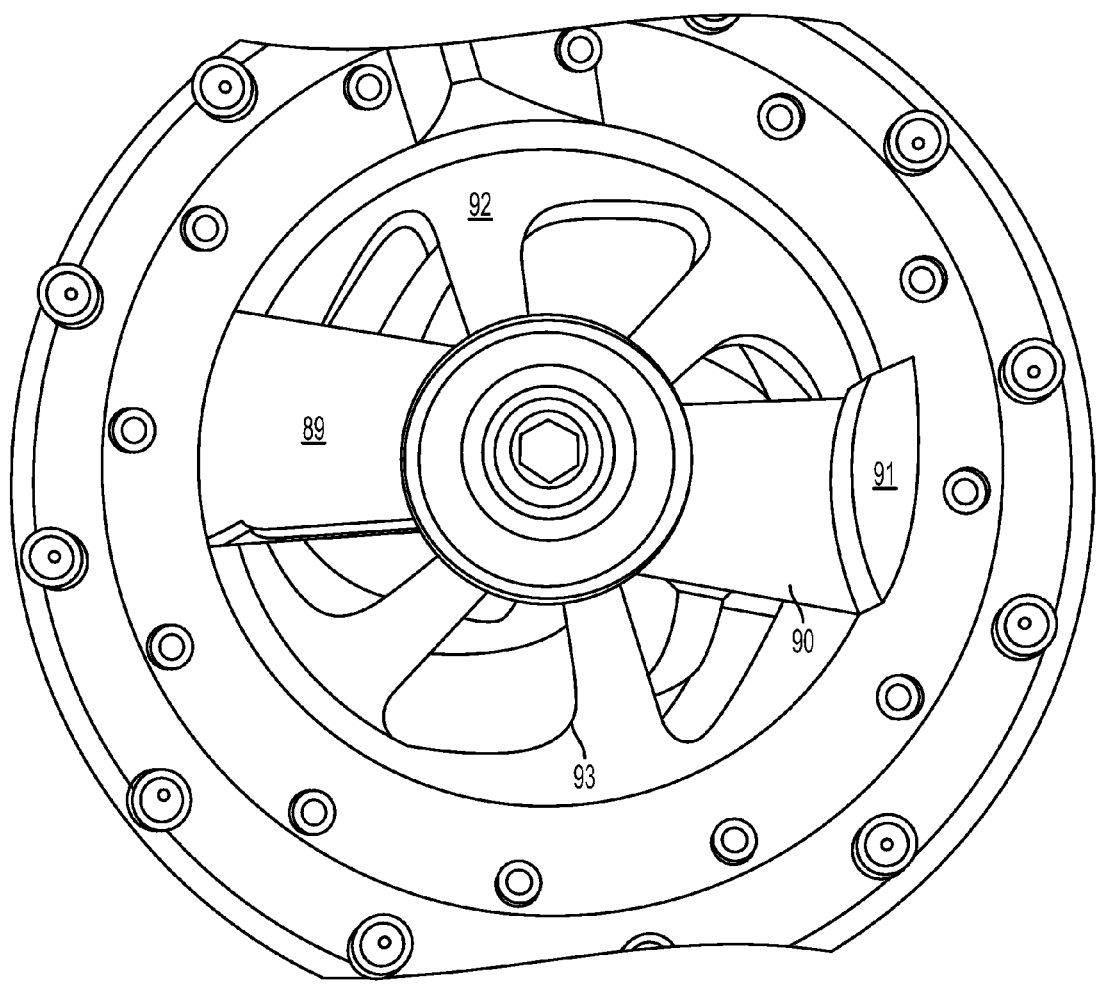
FIG. 9 is a front view of the cutter portion of the cartridge/cartridge/macerator pump, according to an embodiment of the invention.
Figure 10:
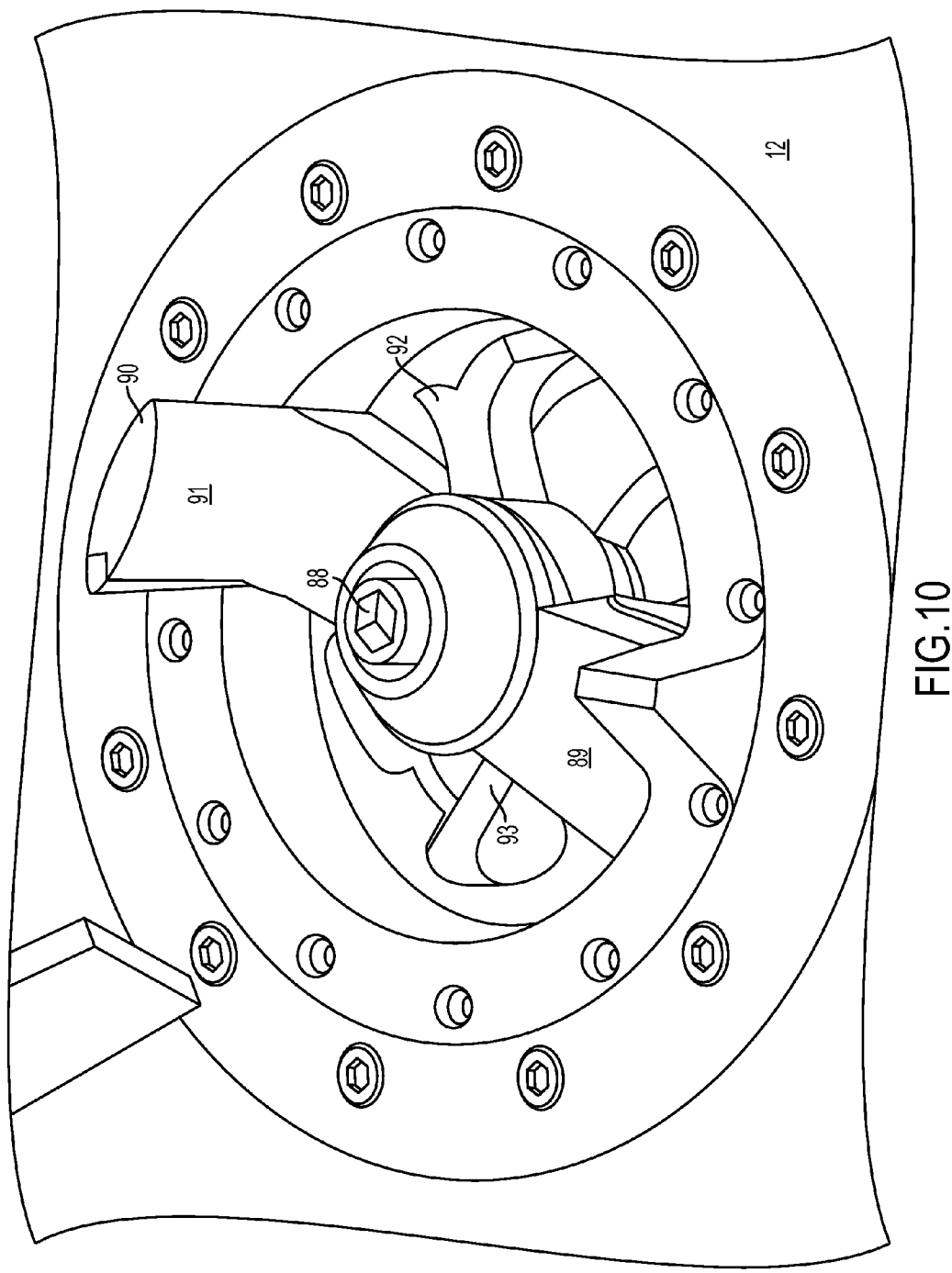
FIG. 10 is a front view of the cutter portion of the cartridge/cartridge/macerator pump assembled within the process tank, according to an embodiment of the present invention.

FIG. 9 is a front view of the cutter portion of the cartridge/macerator pump 22, according to an embodiment of the invention. FIG. 10 is a front view of the cutter portion of the cartridge/macerator pump 22 assembled within the process tank 12, according to an embodiment of the present invention.

Figure 11B:
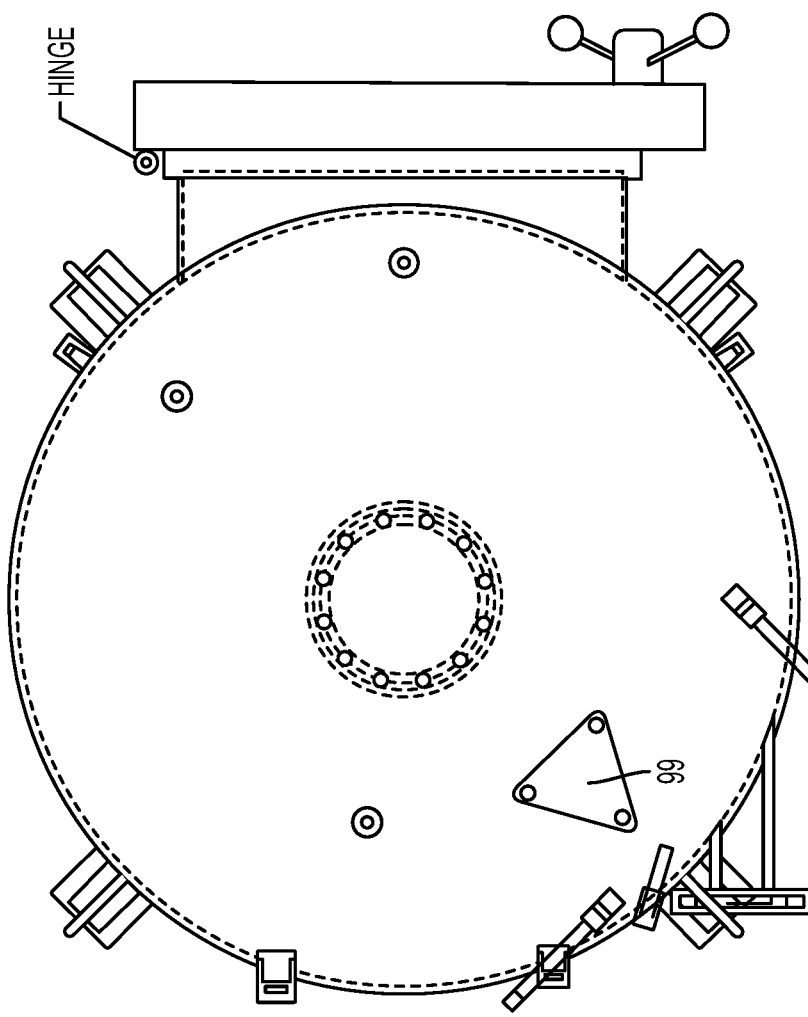

FIGS. 11A-11E depict various views showing the connection of the cartridge/macerator pump 22 to the process tank 12, according to an embodiment of the invention. FIG. 11A shows an elevational view of the process tank 12. In this embodiment, a pump mounting pad 96 may be positioned in the center bottom surface of the process tank 12 for connection with the cartridge system of the cartridge/macerator pump 22. A detail of the pump mounting pad 96 is shown in FIG. 11D. According to one embodiment, the pump mounting pad 96 may have an outer diameter of approximately 10.5 inches and an inner diameter of approximately 9.5 inches. According to another embodiment, the cartridge/macerator pump 22 is mounted to the bottom of the pump mounting pad 96. The position of the pump mounting pad 96 may allow the slurry to be easily drawn into the cartridge/macerator pump 22.

Figure 11C:
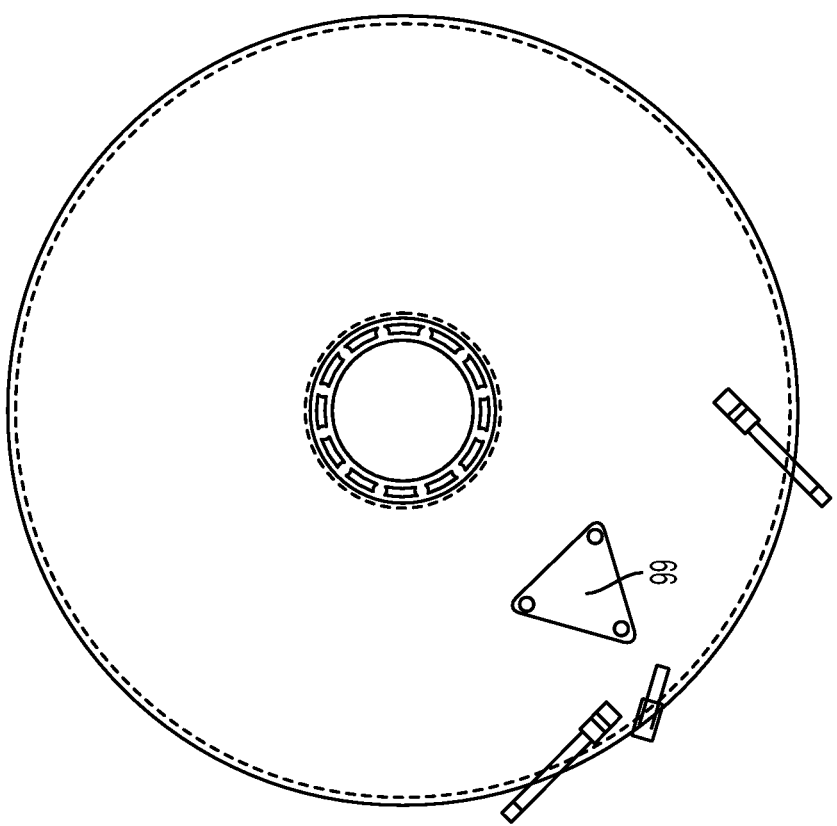
Figure 11E:
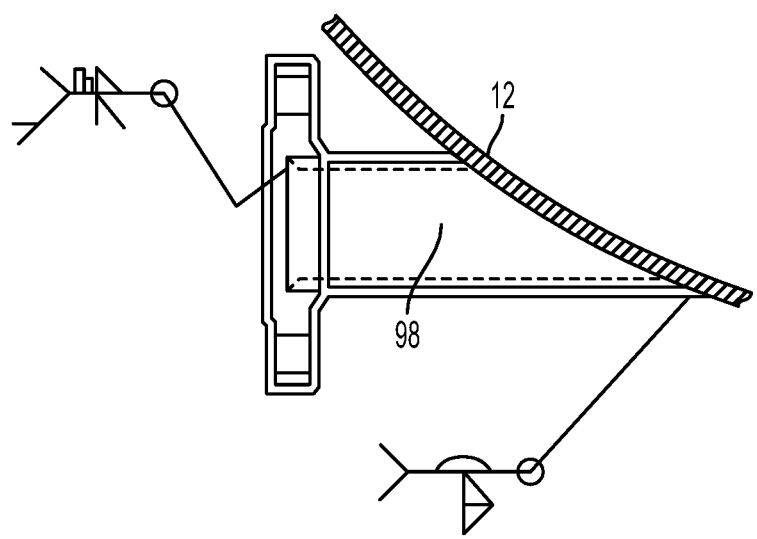

A recirculation connection 98 may be positioned in a side wall or shell of the process tank 12. The recirculation connection 98 may be connected to the recirculation loop 25 downstream of the cartridge/macerator pump 22. The recirculation connection 98 may be centered in height along the vertical wall of the process tank 12 or slightly below center. The recirculation connection 98 may be positioned slightly off-center from the door 16. The positioning of the recirculation connection 98 may allow the slurry to drop down into the process tank 12 towards the pump mounting pad 96 and, thus, into the cartridge/macerator pump 22. A detail of the recirculation connection 98 is shown in FIG. 11E.

A deflector mounting plate 99 may be mounted to the bottom surface of the process tank 12 to push or deflect the re-circulated slurry or debris back into the cartridge/macerator pump 22. In one embodiment, the deflector mounting plate 99 may be positioned substantially below the recirculation connection 98 to receive the re-circulated slurry returning into the process tank 12. In another embodiment, the deflector mounting plate 99 may be tilted or otherwise arranged to deflect a pre-determined amount of slurry back into the cartridge/macerator pump 22. The approximate positioning of the deflector mounting plate is shown in FIGS. 11B and 11C.

According to another embodiment, the OSS 100 may follow one or more of the following method steps to initialize and carry out the ozone sterilization of the RMW 10: 1) "Ready-to-Start," the bags of waste material are loaded into the process tank and ready for the door to be closed and the machine started; 2) "Ozonate," ozone and water is recirculated in the process tank; 3) "Grind, Recirculate, and Sterilize," the waste material is ground and recirculated with ozone until the waste debris are sterilized; 4) "Cool Down and Discharge," the ground and sterilized waste is cooled down with fresh water and discharged into the filter separator; "Drain and Dispose," water from the cooled process is drained in a sanitary sewer, while unrecognizable, sterile remains are ready for disposal in regular trash; and "Confirmation," a computer prints a receipt verifying the process and stores results in a history record.

Figure 12:
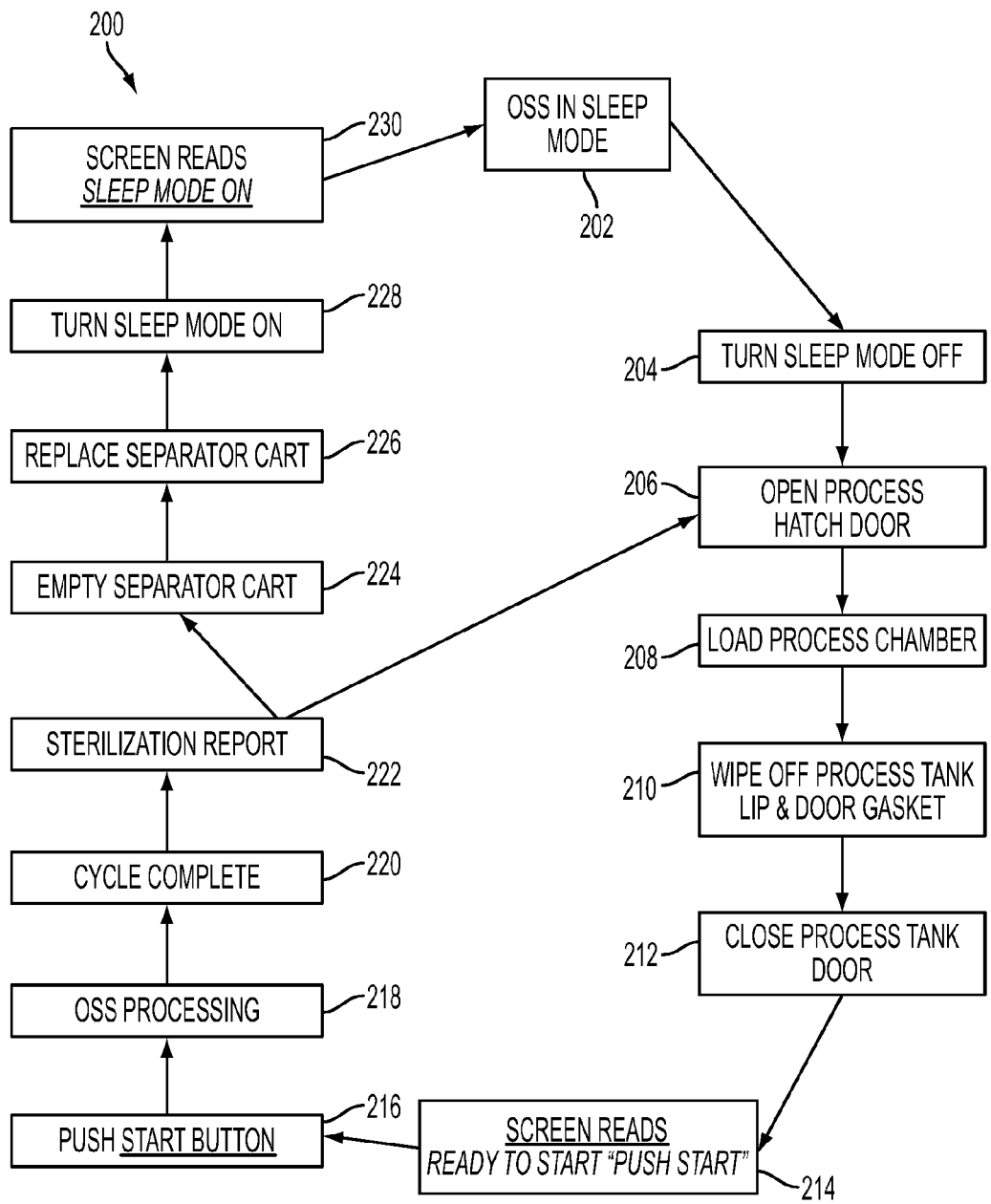
FIG. 12 is a block diagram of the operations method of the ozone sterilization system according to an embodiment of the present invention.

FIG. 12 is a block diagram of the operation method 200 of the ozone sterilization system 100 according to one embodiment of the present invention. In this embodiment, the OSS 100 may begin in sleep mode 202. After turning the sleep mode off 204, an operator may open the process hatch door 206, load the process tank 208, wipe off the process tank lip and door gasket 210 and close the process tank door 212. A display screen of the operations system 26 may read "Ready for start: PUSH START" 214. The operator may then push the start button 216, wherein the operations system 26 may start OSS processing 218. Once the sterilization cycle is complete 220, the operations system 26 may compile and produce a sterilization report 222. The operations system 26 may signal the operator to open the process tank door 206 and empty the separator cart 224. The operator may then replace the separator cart 226 and the operations system 26 may return to sleep mode 228. During sleep mode 228, the display screen may read "Sleep mode ON" 230.

According to another embodiment, during start-up of the OSS 100, an operator may use the operating system 26 to confirm that all of the system parameters are prepared properly on a screen display. The start parameters may include an ozone system check, a check of various safety features, including, but not limited to, that the process tank door 16 is closed and secured, a cold water temperature sensor check, and an electricity check. Once these start parameters have been satisfied, a start button may be pressed, and operation of the OSS 100 may be engaged.

According to one embodiment, there may be no further human operator intervention in the process after the start button is pressed until the sterilization cycle is completed.

According to another embodiment, the operator may be required to move away from the immediate vicinity of the OSS 100.

FIG. 13 is a chart 300 showing control stages of the ozone sterilization system according to an embodiment of the present invention. In this embodiment, the initial stage 302 initializes the ozone generator to produce ozonated water. In the sleep stage 304 the unit remains locked so that it cannot be started. The sleep stage 304 recovers to the initial stage 302. In the ready-to-start stage 306 the unit is made ready for the process tank door to be closed and the start button to be pushed. The ready-to-start stage 306 recovers to the initial stage 302. The ozonate stage 308 fills the process tank with the ozonated water and ozone gas. The fill stage 310 fills the process tank with ozonated water. The grind stage 312 chops and recirculates the waste and the ozonated water through the process tank. The sterilize stage 314 calculates the sterilization time based on the ozone concentration and the time as material continues to be circulated. The venting stage 316 vents air from the process tank to the atmosphere. The discharge stage 318 discharges the contents of the process tank into the separator. The rinse stage 320 rinses the process tank with water from the facility. The drain stage 322 drains the process tank and the filter separator. The complete stage 324 prints a report and stores a history of the sterilization process.

The principles of the invention may be applied to the treatment of water soluble polymeric or fibrous waste materials, whereby treatment results in the dissolution of the waste material. The system may be used without any changes to achieve the dissolution of this waste material, as opposed to biological neutralization. In operation, the waste to be processed may be water soluble polymeric or fibrous waste material. Circulation within the closed waste processing system results in the dissolution of the waste material. Water dissolvable materials dissolve below boiling temperature. Thus, processing temperatures for dissolving the water soluble polymeric or fibrous waste material range from about 85° F. to about 165° F. Since temperatures below the boiling point of water are used, the treatment may be performed at lower pressure. A suitable pressure range may be, for example, from about 5 to about 25 PSI. The circuit components of the system for this specific use are formed from suitable materials that are capable of withstanding the temperature, pressure and abrasion associated with the operation of the waste processing system for treating water soluble polymeric or fibrous waste material. Since lower temperatures and pressures are used in this embodiment as opposed to biological neutralization, different kinds of material, known to a skilled artisan, may be used for the circuit components than are used for biological neutralization. The treatment of the water soluble polymeric or fibrous waste material according to the present invention results in the dissolution of the material. The processed liquid may be discharged into, for example, a municipal sewer system.

Ozone concentrations of from 5% to about 50% are used in accordance with embodiments of the present invention. Of course, the particular levels of ozone to be used in the systems and methods according to embodiments of the present invention may depend upon the amount of time the waste slurry is exposed to the ozone.

The ozone sterilization system has many advantages over the prior art. The ozone sterilization system, for example, is a process that uses a single process tank to sterilize waste material, rather than a batch processing system that uses multiple processing tanks. Thus, the OSS is compact and more efficient. The OSS may allow for the recovery of recyclable materials in separate batches. The OSS may treat both solids and liquids together or separately. The OSS may destroy HIPAA and classified paper documents. The OSS may also treat bio-waste laboratory materials, including blood and urine products.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for caring out this disclosure.

We hereby claim:

1. A system for ozone sterilization of waste material, comprising:
a tank including a top surface, a bottom surface and a substantially cylindrical side wall that define a substantially hollow chamber configured to receive waste material, ozonated water, and ozone gas, wherein the tank includes a first inlet to receive the waste material, a second inlet to receive ozonated water and ozone gas, a third inlet to receive the re-circulated slurry, and an outlet to discharge the slurry to the pump, wherein the first, second and third inlets are positioned within the substantially cylindrical side wall and the outlet is positioned within the bottom surface;
an ozone system to generate the ozonated water and coupled to the second inlet;
a pump coupled to the tank to receive the waste material and the ozonated water from the tank and form a slurry, the pump comprising a cutter assembly to reduce a particle size of the slurry through cutting;
a circulation loop coupled between the tank and the pump to receive the slurry from the pump and re-circulate the slurry to the tank until the slurry is sterilized; and
a deflector plate positioned on the bottom surface of the tank at an angle and height to allow recirculation and deflection to guide the slurry from the third inlet to the outlet after re-circulation, wherein the third inlet is positioned behind the deflector plate with respect to the outlet at a height and position to allow recirculation for the circumference of the tank wall.

2. The system of claim 1, further comprising a filter separator to receive the sterilized slurry from the pump and separate a solid portion of disposable waste and a liquid portion of disposable waste from the slurry.

3. The system of claim 1, wherein the pump comprises cartridge device including a cutter, a cutter bar plate and an impeller having cutting surfaces in a stacked formation.

4. The system of claim 3, wherein the cutter bar plate includes fingers to cut on both top and bottom surfaces.

5. The system of claim 3, wherein the cutter bar plate has a surface for vertical cutting with the cutter.

6. The system of claim 3, wherein the cutter includes at least one carbon insert for increased strength durability while cutting the slurry.

7. The system of claim 1, wherein the ozone system includes an ozone generator to generate the ozonated water and ozone gas, and an ozone injection device to inject the ozonated water and ozone gas into the tank via the second inlet.

8. The system of claim 1, wherein the ozonated water has an ozone concentration between approximately 5% and 50%.

9. The system of claim 1, wherein the circulation loop continuously re-circulates the slurry for an amount of time determined based on at least one of the amount of waste material, the type of waste material, the ozone concentration of the slurry, or the temperature of the slurry.

* * * * *